US012605047B2

(12) United States Patent
Torkuhl et al.

(10) Patent No.: US 12,605,047 B2
(45) Date of Patent: Apr. 21, 2026

(54) METHOD OF AFFIXING A WINDOW ON AN ENDOSCOPE AND ENDOSCOPE

(71) Applicant: OLYMPUS Winter & Ibe GmbH, Hamburg (DE)

(72) Inventors: Nils Torkuhl, Barsbuettel (DE); Uwe Schoeler, Hoisdorf (DE)

(73) Assignee: OLYMPUS Winter & Ibe GmbH, Hamburg (DE)

( * ) Notice: Subject to any disclaimer, the term of this patent is extended or adjusted under 35 U.S.C. 154(b) by 137 days.

(21) Appl. No.: 18/642,082

(22) Filed: Apr. 22, 2024

(65) Prior Publication Data

US 2024/0358235 A1     Oct. 31, 2024

Related U.S. Application Data

(60) Provisional application No. 63/462,593, filed on Apr. 28, 2023.

(51) Int. Cl.
*A61B 1/00*          (2006.01)

(52) U.S. Cl.
CPC ........ *A61B 1/0011* (2013.01); *A61B 1/00096* (2013.01)

(58) Field of Classification Search
CPC .............. A61B 1/0011; A61B 1/00096; A61B 1/00097; A61B 1/00117; A61B 1/00195; A61B 1/055; G02B 23/2423
See application file for complete search history.

(56) References Cited

U.S. PATENT DOCUMENTS

2020/0305683 A1    10/2020   Schoeler et al.

*Primary Examiner* — Timothy J Neal
(74) *Attorney, Agent, or Firm* — Scully, Scott, Murphy & Presser, P.C.

(57)          ABSTRACT

A method of affixing a window on an endoscope. The method including positioning the window on or in an end part of the endoscope and creating a bezel for the window by overmoulding a lateral edge of the window with amorphous metal.

13 Claims, 2 Drawing Sheets

METHOD OF AFFIXING A WINDOW ON AN ENDOSCOPE AND ENDOSCOPE

CROSS-REFERENCE TO RELATED APPLICATION

The present application is based upon and claims the benefit of priority from U.S. Provisional Application No. 63/462,593 filed on Apr. 28, 2023, the entire contents of which is incorporated herein by reference.

BACKGROUND

Field

The present disclosure relates to a method of affixing a window on an endoscope and an endoscope.

Prior Art

Endoscopes used in medical applications are typically hermetically isolated from their surroundings at the distal tip by means of a window that is affixed on the distal end of the endoscope shaft or inside the endoscope shaft near the distal tip in a hermetically sealing way. In the case of endoscopes having a proximal ocular end with an ocular lens and an ocular cone for attachment of a camera head or for direct eye view by a medical practitioner, the proximal end may likewise be hermetically sealed by a proximal window. The windows render the endoscopes able to be autoclaved, cleaned and sterilized for repeated use without washing fluids or any moisture entering the interior of the endoscopes.

Such windows are typically made from sapphire and are hermetically connected to the endoscope in a two-step process involving gluing or soldering from the proximal end for producing a good connection and soldering from the distal end for producing a hermetic seal. Other methods of inserting a sapphire window comprise soldering in the sapphire disc from both sides or gluing the sapphire disc into a sleeve and soldering the sleeve into the shaft tube. Soldering may also be used for the proximal end.

It is known to produce hermetic seals by metallizing, in particular gold-plating, the cylindrical side wall of the window in a multi-layered process, then inserting it into the tube and to solder it to the surrounding tube material. This is a relatively complex process. Moreover, it is required to use a solder that will not be corroded by corrosive chemicals used to clean the endoscope.

The socket for the window, i.e., the fiber tube tip representing the joining partner during soldering, must also to be plated with gold. For diameters smaller than 5.4 mm, the soldering process is performed with a soldering iron, and with induction for larger diameters. The sapphire window is inserted from distally. The soldering must be sound, otherwise the disc would be in danger of falling out.

For the gluing at its proximal end, the sapphire disc does not have to be coated. However, there is further design complexity involved here, including the use of dry rings and locknuts.

The process as outlined has several drawbacks. Since it is done by hand, it cannot be validated thoroughly. The design carries the danger of the window falling out. The test of the hermeticity of the seal requires a 100% leakage test and works only up to a point. The cleaning of particles and in particular of flux agents in the geometries is difficult, as these lie below the edge of the flat glass support. The fiber tube tip and the sapphire disc edge have to be gold-plated, which doubles the price, in particular in the case of the sapphire discs, and is logistically involved. The costs of soldering with soldering preparation, including reworking the seat of the glass sheet, as well as the consumption of gold solder and cleaning from the aggressive flux agents are high.

In the case of the proximal windows, there is additional constructive effort involved for guaranteeing absolute dryness in the optical system. The high amount of parts also leads to higher costs.

In US 2020/0305683 A1, a method for manufacturing an endoscope is described, detailing the above-described soldering process. A window having a lateral peripheral surface and a flat surface is provided with a metal coating on a lateral peripheral surface and/or an edge region of the flat surface, as well as with a solder preform on a flat surface. The window is inserted into a window seat of an endoscope shaft of the endoscope. Subsequent to the inserting, the solder preform is heated with a heating device such that solder material of the solder preform is distributed between the window and the window seat and, after the solder material cools, solder is arranged between the window and the window seat.

SUMMARY

In light of this, an object is to provide a method of affixing a window on an endoscope and a respective endoscope that avoids the above-mentioned drawbacks.

Such object can be solved by a method of affixing a window on an endoscope, the method including positioning the window on or in an end part of the endoscope and creating a bezel for the window by overmoulding the lateral edge of the window with amorphous metal.

Amorphous metals are known. They are produced from certain alloys by rapid cooling. The melt is subcooled, the rapid cooling freezing the disordered, amorphous atomic structure of the melt in place. The physical properties of amorphous metals differ significantly from those of conventional metals and alloys having periodic crystal structures. In the context of the present disclosure, amorphous alloys, for example, having zirconium or copper as majority component can be used. However, other amorphous alloys having other majority components may be equally used. Criteria for the choice of alloy may be, among others, corrosion resistance under repeated cleaning (chemical or thermal reprocessing) of the endoscopes, or their flowability. Manufacturers of amorphous alloys such as Amorphous Metal Solutions GmbH in Germany or Liquidmetal® Technologies, Inc. in the United States offer various amorphous alloy compositions that lend themselves to the present method and device.

The overmoulding process is generally similar to plastic overmoulding. In the present case, a mould is filled with amorphous metal. However, in this case, the process can be done in vacuum.

In embodiments, the end part of the endoscope is a distal end portion of a shaft of the endoscope, such as a fiber tube tip, or a proximal ocular end part of the endoscope. The window may be a sapphire disc.

After the overmoulding, the lateral edge of the window is surrounded with the amorphous metal, which thereby realizes both the function of creating the connection and of providing a hermitic seal, that have previously been provided by the combination of gluing and soldering. During its cooling off, the amorphous metal undergoes minimal shrinkage, thereby tightly surrounding the sapphire window and providing a tight seal without bursting the sapphire window. Because of this, tolerances in the various parts can be met.

In embodiments, the overmoulding can be performed with the window being positioned inside a hollow portion in the end part of the endoscope adjacent to a portion with narrowed inner diameter, causing the amorphous metal to assume a shape that overlaps a distal end face of the window as well as a proximal end face of the window.

The method according to the present disclosure provides a cost advantage and allows the configuration to be such that the window cannot fall out, since the amorphous metal can provide rings protruding over the edges of the proximal and distal services of the window, holding it back from moving either proximally or distally. Since the high degree of mechanical sturdiness is assured intrinsically by the manner of producing the seat, only its hermiticity or proofness against leakage have to be tested.

The end part of the endoscope may be a fiber tube tip, the fiber tube tip can be configured to overlap a fiber tube, and the amorphous metal may be through-welded or soldered. This lowers the requirements for the condition of the edges respect to butt welding and leads to a reduction of errors in the process.

In embodiments, creating the bezel can encompass establishing a material bond between a coated surface of the window and the amorphous metal.

Such object can also be solved by an endoscope having a bezel and a window, the window being affixed on or in an end part of the endoscope by the bezel, wherein the bezel comprises amorphous metal overmoulded over the window. The endoscope having a window surrounded by a bezel of overmoulded amorphous metal has the same features, characteristics and advantages as were described hereinabove.

In embodiments, the end part of the endoscope can be a distal end portion of a shaft of the endoscope, such as a fiber tube tip, or a proximal ocular end part of the endoscope. The window may be a sapphire disc.

In further embodiments, the amorphous metal can have a shape overlapping a distal end face of the window as well as a proximal end face of the window. With this, the bezel can be shaped such as to keep the window in place and preventing it from sliding in the axial direction of endoscope, either proximally or distally.

The bezel can have a material bond between a coated surface of the window and the amorphous metal in embodiments. The material bond can provide a tight seal of the window inside the endoscope.

BRIEF DESCRIPTION OF THE DRAWINGS

Further features will become evident from the description of embodiments, together with the claims and the appended drawings. Embodiments can fulfill individual features or a combination of several features.

The embodiments described below, without restricting the general intent of the invention, based on exemplary embodiments, wherein reference is made expressly to the drawings with regard to the disclosure of all details that are not explained in greater detail in the text.

In the drawings:

FIG. 1 illustrates an embodiment of a fiber tube tip at the distal end of an endoscope shaft of an endoscope having a bezel made from amorphous metal, FIG. 2 illustrates another embodiment of an endoscope, FIG. 3 illustrates a simplified third embodiment; and FIG. 4 illustrates schematically an embodiment of an endoscope.

In the drawings, the same or similar types of elements or respectively corresponding parts are provided with the same reference numbers in order to prevent the item from needing to be reintroduced.

DETAILED DESCRIPTION

Figures 1, 2, 3:
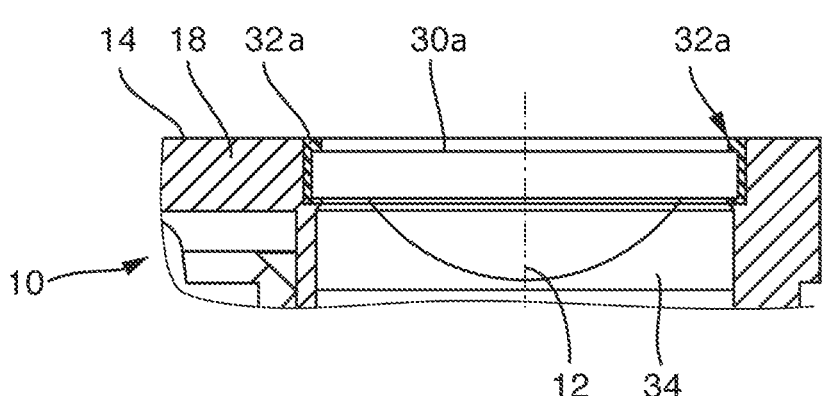

The distal end part 14 of the shaft of an endoscope 10 in the form of a fiber tube tip 18 is illustrated in FIG. 1. Centered around optical axis 12 of the hollow endoscope shaft, a distal window 30a made from sapphire and having a flat cylindrical shape is inserted at the distal end. is The distal window 30a is held within the shaft by means of a distal bezel 32a, which has been overmoulded circumferentially around the periphery of the distal window 30a in a way that it overlaps the flat distal and proximal services of the distal window 30a by a small degree, thus keeping the distal window 30a in place and hindering it from moving either distally or proximately out of position. Cooling of the amorphous metal after the overmoulding process causes the amorphous metal to contract slightly and thereby clamp the distal window 30a tightly without cracking it. Through the tight clamping, a hermetic seal is created, both with respect to the boundary between the distal window 30a and distal bezel 32a and between the inner wall of the distal end part 14 and the distal bezel 32a. An entry lens 34, in the case shown in the embodiment of FIG. 1, a plano-concave entry lens, can be positioned proximal to the distal window 30a before or after inserting the distal window 30a.

The process of overmoulding may be carried out as an insert molding, wherein the sapphire disc is first placed into the opened mold. After the mold is closed, the mold fixates the sapphire disc in position and the metal melt may be inserted. The metal melt flows around the sapphire disc and creates a hermetic joint. The cooling may be done inside a vacuum chamber. The appropriate cooling rate may depend on the chosen alloy composition and be determined by a series of simple trials.

FIG. 2 illustrates a cross-sectional view through the distal end part 14 of an endoscope shaft of an endoscope 10 centered around optical axis 12. The distal end part 14 of the endoscope shaft comprises two parts, namely the fiber tube 16 providing the main part of the endoscope shaft and a fiber tube tip 18 providing the distal end of the endoscope shaft. The fiber tube tip 18 has an outer structure at its proximal end accommodating the distal end of fiber tube 16, which provides the opportunity for through welding the fiber tube 16 to the fiber tube tip 18.

Fiber tube tip 18 furthermore has an inner circumference providing an annular ledge 20 against which the distal window 30a can be positioned in order to be overmoulded with amorphous metal for creating a distal bezel 32a as illustrated in FIG. 1. The proximal surface of the ledge 20 can be used to position and fix an entry lens 34 of an optical system of the endoscope, such as is also shown in FIG. 1.

The fiber tube tip 18 of the embodiments shown in FIG. 3 comprises an annular recess 22 into which amorphous metal can be injected in order to create the distal bezel 32a around the distal window 30a. Only the outer surface of the distal bezel 32a is shown in FIG. 3.

Figure 4:
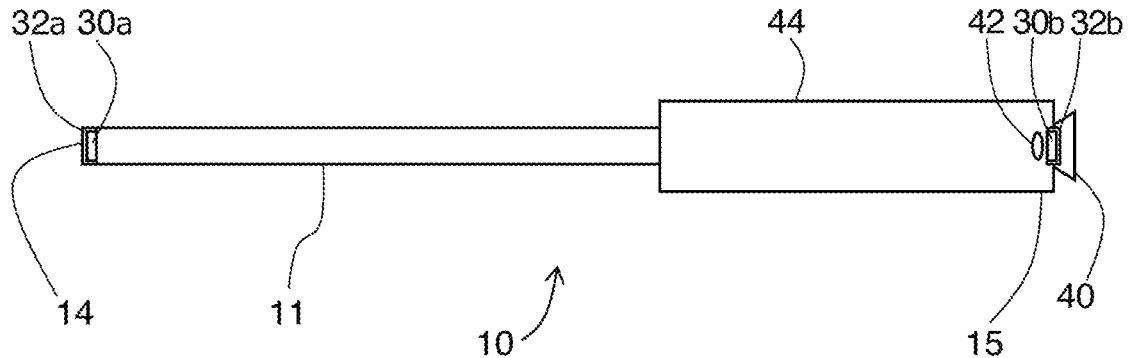

FIG. 4 illustrates schematically an embodiment of an endoscope 10 having a shaft 11 and a grip part 44. At the distal end part 14 of the shaft 11, the shaft 11 is sealed by a distal window 30a fixed to the inside of the shaft 11 by a distal bezel 32a according to the present disclosure, formed by overmoulding a lateral edge of the distal window 30a with amorphous metal, such as is illustrated, for example, in FIG. 1 or FIG. 3. The handle or grip part 44 ends in a proximal end part 15 of the endoscope 10 in an ocular cone 40 having an ocular lens 42. The opening provided for light exiting the endoscope 10 proximally in the center of the ocular cone 40 may also be sealed by a proximal window 30b that is, similarly to the distal window 30a, held in a proximal bezel 32b according to the present disclosure, formed by overmoulding a lateral edge of the proximal window 30b with amorphous metal.

While there has been shown and described what is considered to be embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE SIGNS

10 Endoscope
11 Shaft
12 optical axis
14 distal end part
15 proximal end part
16 fiber tube
18 fiber tube tip
20 annular ledge
22 annular recess
24 welding region
30a distal window
30b proximal window
32a distal bezel
32b proximal bezel
34 entry lens
40 ocular cone
42 ocular lens
44 grip part

The invention claimed is:

1. A method of affixing a window on an endoscope, the method comprising:
   positioning the window on or in an end part of the endoscope; and
   creating a bezel for the window by overmoulding a lateral edge of the window with amorphous metal.

2. The method according to claim 1, wherein the end part of the endoscope is a distal end portion of a shaft of the endoscope.

3. The method according to claim 1, wherein the end part of the endoscope is one of a fiber tube tip or a proximal ocular end part of the endoscope.

4. The method according to claim 1, wherein the window is a sapphire disc.

5. The method according to claim 1, wherein the overmoulding is performed with the window positioned inside a hollow portion in the end part of the endoscope adjacent to a portion with a narrowed inner diameter, causing the amorphous metal to assume a shape that overlaps a distal end face of the window and overlaps a proximal end face of the window.

6. The method according to claim 1, wherein the end part of the endoscope is a fiber tube tip, the fiber tube tip is configured to overlap a fiber tube, and the method further comprising one of through-welding or soldering the amorphous metal.

7. The method according to claim 1, wherein the creating of the bezel comprises establishing a material bond between a coated surface of the window and the amorphous metal.

8. An endoscope comprising:
   a bezel; and
   a window,
   wherein the window is affixed on or in an end part of the endoscope by the bezel, and the bezel comprises amorphous metal overmoulded over the window.

9. The endoscope according to claim 8, wherein the end part of the endoscope is a distal end portion of a shaft of the endoscope.

10. The endoscope according to claim 8, wherein the end part of the endoscope is one of a fiber tube tip or a proximal ocular end part of the endoscope.

11. The endoscope according to claim 8, wherein the window is a sapphire disc.

12. The endoscope according to claim 8, wherein the amorphous metal having a shape overlapping a distal end face of the window and overlapping a proximal end face of the window.

13. The endoscope according to claim 8, wherein the bezel having a material bond between a coated surface of the window and the amorphous metal.

* * * * *